United States Patent [19]
Wuest et al.

[11] Patent Number: 5,475,017
[45] Date of Patent: Dec. 12, 1995

[54] DIARYL-SUBSTITUTED HETEROCYCLIC COMPOUNDS, DRUGS AND COSMETICS OBTAINED THEREFROM

[75] Inventors: Hans-Heiner Wuest, Dossenheim; Bernd Janssen, Ludwigshafen, both of Germany; William V. Murray, Belle Mead, N.J.; Michael P. Wachter, Bloomsbury, N.J.; Stanley Bell, Narbeth, Pa.

[73] Assignee: BASF Aktiengesellschaft, Ludwigshafen, Germany

[21] Appl. No.: 242,415

[22] Filed: May 13, 1994

Related U.S. Application Data

[62] Division of Ser. No. 972,518, Nov. 6, 1992, Pat. No. 5,338,749, which is a division of Ser. No. 717,264, Jun. 18, 1991, Pat. No. 5,196,532, which is a division of Ser. No. 476,875, Feb. 8, 1990, Pat. No. 5,061,705.

[30] Foreign Application Priority Data

Feb. 10, 1989 [DE] Germany ............... 39 03 993.5

[51] Int. Cl.$^6$ ............... A61K 31/415; C07D 231/06
[52] U.S. Cl. ............... 514/403; 514/236.5; 514/326; 514/859; 514/861; 514/863; 514/915; 514/844; 546/211; 548/379.7; 544/140; 424/59
[58] Field of Search ............... 548/379.7; 514/403

[56] References Cited

U.S. PATENT DOCUMENTS 5,194,664  3/1993  Wuest et al. .
5,326,900  7/1994  Wuest et al. .

*Primary Examiner*—Robert W. Ramsuer
*Attorney, Agent, or Firm*—Oblon, Spivak, McClelland, Maier & Neustadt

[57] ABSTRACT

Compounds of formula I

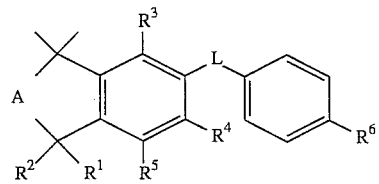

and compounds of formula Ia

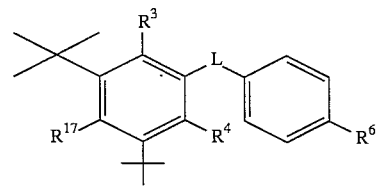

and their physiologically tolerated salts, processes for their preparation and drugs and cosmetics prepared therefrom.

8 Claims, No Drawings

DIARYL-SUBSTITUTED HETEROCYCLIC COMPOUNDS, DRUGS AND COSMETICS OBTAINED THEREFROM

This is a division, of application Ser. No. 07/972,518, filed on Nov. 6, 1992 now U.S. Pat. No. 5,338,749, which is a Divisional of Ser. No. 07/717,264 filed Jun. 18, 1991 now U.S. Pat. No. 5,196,532 which is a Divisional of Ser. No. 07/476,875 filed Feb. 8, 1990 now U.S. Pat. No. 5,061,705.

The present invention relates to novel diaryl-substituted five-membered or six-membered heterocyclic compounds, processes for their preparation and their use in the prophylaxis and treatment of disorders.

U.S. Pat. No. 4,326,055 and CA 1 183 541 disclose that retinoidal benzoic acid derivatives have pharmacological actions in the topical and systemic therapy of neoplasias and dermatoses, for example acne or psoriasis. The disadvantage of these compounds is their low therapeutic index with regard to the side effects summarized by the term hypervitaminosis A.

We have found that compounds of the general formula I

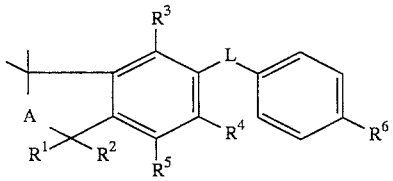

where

A is an ethylene or methylene radical which is unsubstituted or substituted by methyl, hydroxyl or oxo, L is a saturated or unsaturated five-membered or six-membered heterocyclic structure which is unsubstituted or substituted by hydroxyl, mercapto, $C_1$-$C_6$-alkyl, or $C_1$-$C_4$-alkanoyl and has from 1 to 3 heteroatoms from the group consisting of N, O and S, the second and third being a nitrogen atom, $R^1$ and $R^2$ are each hydrogen or methyl, $R^3$ is hydrogen, hydroxyl or $C_1$-$C_6$-alkoxy, $R^4$ is hydrogen, $C_1$-$C_4$-alkyl, halogen, preferably fluorine, or methoxy, $R^5$ is hydrogen or methoxy and $R^6$ is hydrogen, methyl, nitrile or a $C_2$-$C_{10}$-ketal group of the formula

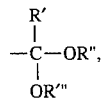

where R', R" and R''' are each alkyl of 1 to 9 carbon atoms, the sum of the carbon atoms of R', R" and R''' is from 2 to 10 and R' may furthermore be hydrogen, or a radical —$CHR^7$—$OR^8$, —$CHR^7$—$NR^9R^{10}$, —$COR^{11}$, —$SR^{12}$, —$SR^{12}$,

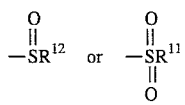

where $R^7$ is hydrogen or $C_1$-$C_4$-alkyl, $R^8$ is hydrogen, $C_1$-$C_4$-alkyl, $C_1$-$C_{20}$-alkanoyl or unsubstituted or substituted benzoyl, $R^9$ and $R^{10}$ are each hydrogen, $C_1$-$C_4$-alkyl, $C_1$-$C_6$-alkanoyl or unsubstituted or substituted benzoyl or, together with the nitrogen atom to which they are bonded, form a heterocyclic radical, $R^{11}$ is hydrogen, $C_1$-$C_4$-alkyl or a radical —$OR^{13}$ or —$NR^{14}R^{15}$, where $R^{13}$ is hydrogen, unsubstituted or hydroxyl-substituted $C_1$-$C_8$-alkyl, unsubstituted or substituted aryl or aralkyl which is unsubstituted or-substituted in the aryl moiety, and where $R^{14}$ and $R^{15}$ are each hydrogen, unsubstituted or hydroxyl-substituted $C_1$-$C_6$-alkyl or unsubstituted or substituted aralkyl or aryl, or $R^{14}$ and $R^{15}$, together with the nitrogen atom to which they are bonded, form a heterocyclic radical, and $R^{12}$ is $C_1$-$C_4$-alkyl, and compounds of formula Ia

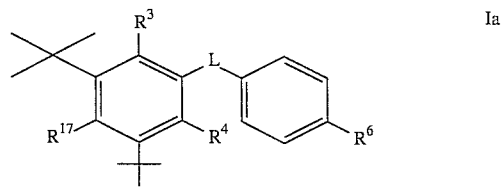

where $R^3$, $R^4$, $R^6$ and L have the abovementioned meanings and $R^{17}$ is hydrogen or hydroxyl, and their physiologically tolerated salts have an improved action profile, especially with regard to the side effects.

Preferred heterocyclic radicals L are the following structures:

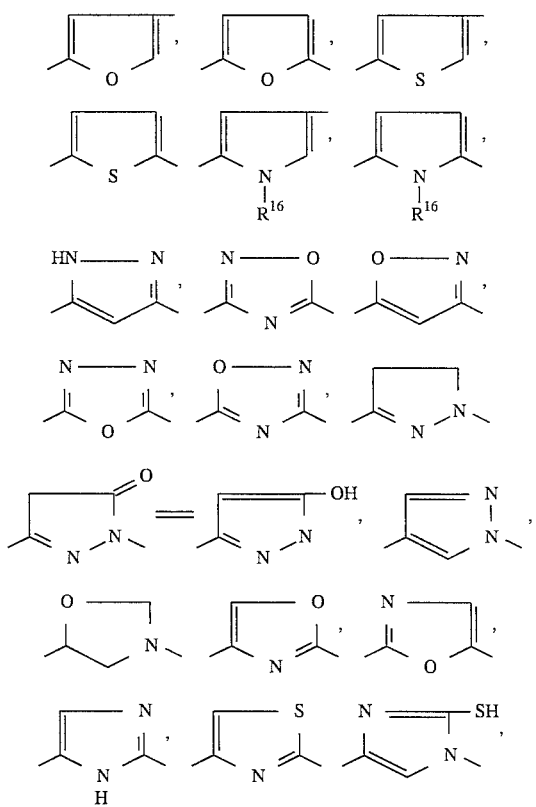

-continued

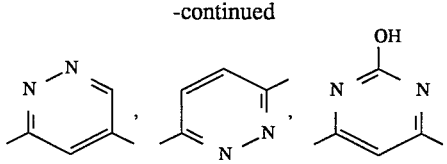

where $R^{16}$ is hydrogen, $C_1$-$C_6$-alkyl or $C_1$-$C_4$-alkanoyl.

Suitable heterocyclic radicals —$NR^9R^{10}$ and —$NR^{14}R^{15}$ are, in particular, pyrrolidino, piperidino and morpholino. Preferred substituents of the benzoyl group ($R^8$, $R^9$ and $R^{10}$) are methoxy, nitro and methyl as well as halogen, in particular chlorine or bromine. Preferred aryl radicals ($R^{13}$, $R^{14}$ and $R^{15}$) are phenyl which is unsubstituted or substituted by methyl, methoxy or nitro. Preferred aralkyl groups ($R^{13}$, $R^{14}$ and $R^{15}$) are benzyl which may be substituted in the moiety part in particular by methyl or methoxy or halogen, preferably chlorine or bromine.

The novel compounds of the formula I can be prepared by methods known in principle for the synthesis of heterocycles. An overview is given in, for example, Comprehensive Heterocyclic Chemistry (Eds. A. R. Katritzky and C. W. Rees), Vol. 1–8, Pergamon Press, 1984.

The following processes are preferably used:

a) Reaction of a 1,3-diketo compound of the formula II

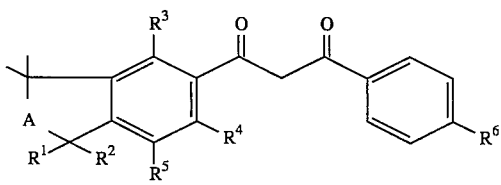

where A and $R^1$-$R^6$ have the abovementioned meanings, with hydrazine, hydroxylamine or urea to give the corresponding pyrazole, isoxazole or 2-hydroxypyrimidine; this reaction can obviously be varied, for example by the phenyl nucleus substituted by $R^6$ being bonded from the outset to an N atom of the hydrazine, of the hydroxylamine or of the urea. In formula II, for example, a lower alkoxy radical then occupies its position.

b) Reaction of a 1,4-diketo compound of the formula III or of a ketal of the formula IV

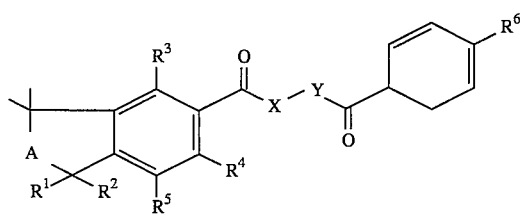

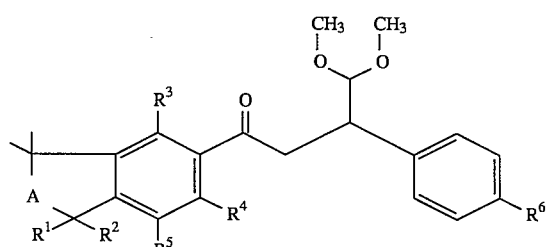

where A and $R^1$-$R^6$ have the abovementioned meanings and X and Y in formula III are each —$CH_2$— or —NH—, with a dehydrating agent, if necessary together with a sulfide or hydrogen sulfide, ammonia or ammonium salt, a primary amine or hydrazine to give the corresponding furan, thiophene, pyrrole, pyridazine, oxazole or 1,3,4-oxadiazole;

c) Reaction of a carboxylic acid derivative of the formula V or VI

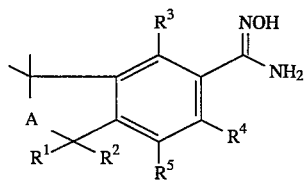

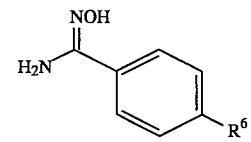

where A and $R^1$ to $R^6$ have the abovementioned meanings, with another carboxylic acid derivative of the formula VII or VIII

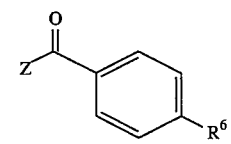

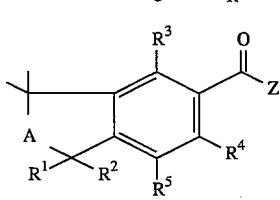

where A and $R^1$ to $R^6$ have the abovementioned meanings and Z is chlorine, $C_1$-$C_4$-alkoxy or hydroxyl, under the conditions of a cyclization reaction with conventional dehydration;

d) 1,3-Dipolar cycloaddition of a nitrile oxide of the formula IX

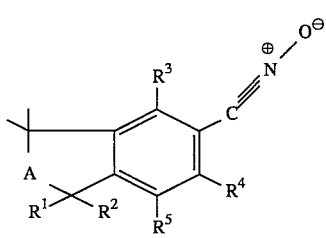

where A and $R^1$-$R^5$ have the abovementioned meanings, with a monoarylacetylene of the formula X

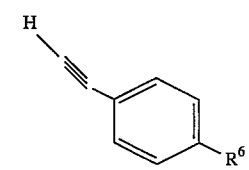

where $R^6$ has the abovementioned meanings, to give an isoxazole of the formula I;

e) Methods which convert the compounds described under a)–d) or prepared by other processes into further novel compounds of the formula I by conventional transformation of the radical $R^6$.

The processes according to a)–c) are condensation reactions which are known in principle and in some cases take place without the addition of a catalyst but are preferably catalyzed by a base or acid, which advantageously is simultaneously used as the dehydrating agent. Preferably used agents of this type are mineral acids, such as hydrochloric acid, sulfuric acid or polyphosphoric acid, organic acids, such as glacial acetic acid, Lewis acids, such as phosphorous oxytrichloride, phosphorus pentachloride, tetraphosphorous decaoxide, thionyl chloride or boron trifluoride diethyl etherate, or bases, such as sodium hydroxide, potassium hydroxide, potassium carbonate, sodium bicarbonate, sodium methylate or potassium tert-butylate.

The reactions are advantageously carried out in a suitable solvent at 0°–200° C., preferably at the reflux temperature of the solvent used. Particularly suitable solvents are alcohols, such as methanol, ethanol, isopropanol or n-butanol, aromatic hydrocarbons, such as benzene, toluene or xylene, aprotic dipolar solvents, such as dimethylformamide or dimethyl sulfoxide, or chlorohydrocarbons, such as methylene chloride, chloroform, 1,2-dichloroethane or 1,2,3-trichloroethane.

The nitrile oxides used in the process according to d) are advantageously prepared in situ from the corresponding oximes of the formula XI by oxidation.

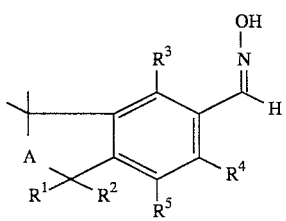

XI

The oxidizing agents used are chlorine, nitrosyl chloride, N-chloro- or N-bromosuccinimide, lead tetraacetate or aqueous hypohalite solutions, preferably sodium hypochlorite solution. If necessary, a base, such as sodium hydroxide solution or triethylamine, is added. The reaction is advantageously carried out in a suitable solvent, for example methylene chloride or dimethylformamide, at from –20° to 70° C., preferably 20°–35° C.

Examples of the methods according to e) include the following:

Benzoates or benzonitriles of the general formula I, where $R^6$ is carboalkoxy or nitrile, can be converted into the free carboxylic acids and their physiologically tolerated salts by hydrolysis. Hydrolysis is preferably carried out in a mixture of a lower aliphatic alcohol, such as methanol, ethanol, propanol, isopropanol or n-butanol, with water in the presence of an alkali metal hydroxide, preferably sodium hydroxide or potassium hydroxide, which is used in excess.

The novel amides can be prepared in a conventional manner by first convening the corresponding benzoic acids into derivatives having a more active carbonyl function, for example into the acyl halides, azides, imidazolides or anhydrides, and treating these with amines $HNR^{14}R^{15}$.

A carboxylic acid, a carboxylate, a carboxamide or a nitrile of the formula I can be reduced to the corresponding alcohols or amines in a conventional manner. Advantageously, the reaction is carried out with the aid of a metal hydride or alkali metal hydride in the presence of a suitable solvent. Preferably used metal hydrides are complex metal hydrides, such as lithium aluminum hydride, lithium borohydride or diisobutylaluminum hydride. Preferred solvents are ethers, such as diethyl ether, tetrahydrofuran, dioxane or 1,2-dimethoxyethane.

An alcohol or amine of the formula I can be acylated in a conventional manner with an alkanoyl or aroyl chloride or anhydride to give the corresponding ester or amide, or alkylated with an alkyl halide, preferably an alkyl bromide or iodide, to give the corresponding ether or more highly alkylated amine, or oxidized with a suitable oxidizing agent, such as manganese(IV) oxide, to give the corresponding aldehyde.

An aldehyde of the formula I can also be obtained by reduction of the corresponding nitrile of the formula I with diisobutylaluminum hydride in a solvent, preferably toluene, hexane or tetrahydrofuran, at from –40° C. to room temperature.

Because of their pharmacological properties, the novel compounds and their physiologically tolerated salts can be used in the topical and systemic therapy and prophylaxis of precancerous conditions and carcinomas of the skin, of the mucus membranes and of the internal organs and in the topical and systemic therapy of ache, psoriasis and other dermatological disorders accompanied by pathological changes in hornification, in particular ichthyosis, Darier's disease, lichen or leucoplakia, or even against eczema, vitiligo, dry eyes and other corneopathias, and for the treatment of rheumatic disorders, in particular those of an inflammatory or degenerative nature, which attack joints, muscles, tendons and other parts of the locomotor system. A preferred indication, in addition to the therapy of dermatological disorders and skin injury due to the action of sunlight or of an iatrogenic nature, for example atrophy induced by corticosteroids, is the prophylaxis of precancerous conditions and tumors.

As cosmetics, the novel compounds can be used for the therapy of injury to the skin by light (embrittlement, creases and wrinkles which are not age-related but due to excessive exposure to UV light or sunlight) and against warts.

The pharmacological actions can be demonstrated, for example, in the test models below. In hamster tracheal tissue in vitro, the novel compounds eliminate keratinization which sets in following vitamin A deficiency. Keratinization is part of the early phase of carcinogenesis, which is inhibited by a similar technique in vivo by the novel compounds of the formula I following initiation by chemical compounds, by high energy radiation or after viral cell transformation. This method is described in Cancer Res. 36 (1972), 964–972 or in Nature 250 (1974), 64–66 and Nature 253 (1975), 47–50.

Furthermore, the novel compounds inhibit the proliferation of certain malignant cells. This method is described in J. Natl. Cancer Inst. 60 (1978), 1035–1041, Experimental Cell Research 117 (1978), 15–22 and Proc. Natl. Acad. Sci. USA 77 (1980), 2937–2940.

The antiarthritic action of the novel compounds can be determined in a conventional manner in an animal experiment using the adjuvant arthritis or streptococcus cell wall-induced arthritis model. The dermatological activity, for example for the treatment of ache, can be demonstrated, inter alia, by the comedolytic activity and the ability to reduce the number of cysts in the Rhino mouse model.

This method is described by L. H. Kligman et al. in The Journal of Investigative Dermatology 73 (1978), 354–358. A further measure of the dermatological activity is the reduction of the sebaceous glands and the associated reduction in sebaceous secretion in the lateral organ of the hamster. This method is described by E. C. Gomez in J. Am. Dermatol. 6 (1982), 746–750.

Furthermore, the reversion of skin injuries caused by UV light, which can be achieved by means of the novel compounds, can be determined in animal models. This method is described by L. H. Kligman et al. in Connect. Tissue Res. 12 (1984), 139–150 and in J. Am. Acad. Dermatol. 15 (1986), 779–785.

The present invention accordingly furthermore relates to therapeutic agents for topical and systemic use and cosmetic agents which contain a compound of the formula I in addition to conventional carriers or diluents and the conventionally used pharmaceutical or cosmetic auxiliaries, in accordance with the desired route of administration and in a dose suitable for the application.

The agents may be administered orally, parenterally or topically. Examples of formulations of this type are tablets, film tablets, coated tablets, capsules, pills, powders, solutions or suspensions, infusion or injection solutions and pastes, ointments, gels, creams, lotions, powders, solutions or emulsions and sprays.

The therapeutic and cosmetic agents may contain the compounds to be used according to the invention in a concentration of from 0.001 to 1%, preferably from 0.001 to 0.1%, for topical administration and preferably in a single dose of from 0.1 to 50 mg in the case of systemic administration, and may be administered daily in one or more doses depending on the nature and severity of the disorders.

The drugs and cosmetics of the invention are prepared in a known manner using the conventional solid or liquid carriers or diluents and the usually used pharmaceutical auxiliaries, in accordance with the desired route of administration and with a suitable dose.

Tablets can be obtained, for example, by mixing the active compound with known auxiliaries, for example inert diluents, such as dextrose, sugar, sorbitol, mannitol or polyvinylpyrrolidone, disintegrants, such as corn starch or alginic acid, binders, such as starch or gelatine, lubricants, such as magnesium stearate or talc, and/or agents for achieving a depot effect, such as carboxypolymethylene, carboxymethylcellulose, cellulose acetate phthalate or polyvinyl acetate. The tablets can also consist of a plurality of layers.

Accordingly, coated tablets can be prepared by coating cores obtained similarly to the tablets with agents conventionally used in tablet coatings, for example polyvinylpyrrolidone or shellac, gum arabic, talc, titanium dioxide or sucrose. The tablet coat, too, may consist of a plurality of layers, and the auxiliaries mentioned above for the tablets can be used.

Solutions or suspensions containing the novel active compound may additionally contain flavor improvers, such as saccharin, cyclamate or sucrose, and, for example, aromas, such as vanillin or orange extract. They may furthermore contain suspending agents, such as sodium carboxymethylcellulose, or preservatives, such as p-hydroxybenzoates. Capsules containing active compounds can be prepared, for example, by mixing the active compound with an inert carrier, such as lactose or sorbitol, and encapsulating the mixture in gelatine capsules.

Examples of advantageous conventional components of cosmetic and pharmaceutical formulations for topical administration are:

anionic, cationic and nonionic emulsifiers and emulsion stabilizers which may simultaneously be consistency adjusters or gel formers, such as polyvinylpyrrolidone, fatty alcohols, glycerol monostearate, polyacrylic acids, cellulose derivatives and ethylene oxide/propylene oxide block polymers, solid or liquid oil components or fats of mineral, vegetable or animal origin, synthetic ester oils, such as glycerol triesters and isopropyl myristate, and hydrophilic components, such as glycerol, polyethylene glycol and propylene glycol.

Examples of other ingredients of cosmetics are light stabilizers, tanning agents, preservatives, antioxidants, pigments, dyes, essential oils and perfume oil, vitamins, plant extracts, collagen, etc. These substances are described in, for example, CTFA, Cosmetic Ingredient Dictionary, 3rd edition, Washington 1982.

Some of the novel compounds have an acidic hydrogen atom and can therefore be converted with bases in a conventional manner into a physiologically tolerated, readily water-soluble salt. Examples of suitable salts are ammonium and alkali metal salts, in particular those of sodium, of potassium and of lithium, and alkaline earth metal salts, in particular those of calcium or of magnesium, and salts with suitable organic bases, such as $C_1$-$C_6$-alkylamines, eg. methylamine, ethylamine or cyclohexylamine, or with substituted $C_1$-$C_6$-alkylamines, in particular hydroxyl-substituted alkylamines, such as diethanolamine, triethanolamine or tris-(hydroxymethyl)aminomethane, and with piperidine or morpholine.

If required, the resulting novel amines of the formula I are converted by known procedures into the addition salt of a physiologically tolerated acid. Examples of suitable conventional physiologically tolerated inorganic acids are hydrochloric acid, hydrobromic acid, phosphoric acid and sulfuric acid, and examples of suitable conventional physiologically tolerated organic acids are maleic acid, fumaric acid, lactic acid, tartaric acid, malic acid, citric acid, salicylic acid, adipic acid and benzoic acid. Further acids are described in Fortschritte der Arzneimittelforschung, Volume 10, pages 224–225, Birkhäuser Verlag, Basle and Stuttgart, 1966.

EXAMPLE 1

4-(4-Carbomethoxyphenyl)-2-(5,6,7,8-tetrahydro-5,5, 8,8-tetramethyl- 2-naphthalenyl)-furan 3-(4-carbomethoxyphenyl)-1-(5,6,7,8-tetrahydro-5,5, 8,8-tetramethyl- 2-naphthalenyl)-prop-2-en-1-one:

138 g (0.6 mole) of 6-acetyl-1,2,3,4-tetrahydro- 1,1,4,4-tetramethylnaphthalene and 98.5 g (0.6 mole) of methyl 4-formylbenzoate in a mixture of 16 g of sodium hydroxide and 690 ml of methanol were stirred for 16 hours at room temperature. The precipitated crystals were filtered off under suction and dried to give 132 g of 3-(4-carbomethoxyphenyl)-1-(5,6,7,8-tetrahydro- 5,5,8,8-tetramethyl-2-naphthalenyl)-prop-2-en-1-one of melting point 89–91° C.

3-(4-Carbomethoxyphenyl)-4-dimethoxy-1-(5,6,7,8-tetrahydro- 5,5,8,8-tetramethyl-2-naphthalenyl)-1-butanone:

47.3 g (126 millimoles) of 3-(4-carbomethoxyphenyl)-1-(5,6,7,8-tetrahydro-5,5,8,8-tetramethyl-2-naphthalenyl)-prop- 2-en-1-one, 360 ml of nitromethane and 4 g of 40% strength methanolic benzyltrimethylammonium hydroxide solution (Triton B) were stirred for 5 hours at room temperature. Thereafter, 850 ml of ether were added, the mixture was washed in succession with 2 N hydrochloric acid, twice with saturated sodium bicarbonate solution and twice with water and once with saturated sodium chloride solution, dried over sodium sulfate and evaporated down. 51.7 g of an oily residue remained; 45 g of this residue were dissolved in 122 ml of methylene chloride and 122 ml of tetrahydrofuran and the solution was added dropwise at −35° C. to 245 ml of a 1 M solution of sodium methylate in methanol.

This solution was added dropwise at −35° C. to a separately prepared mixture of 245 ml of concentrated sulfuric acid and 920 ml of methanol (the sulfuric acid was added dropwise at −35° C. to the methanol). The mixture was stirred for 0.5 hour at −35° C., then allowed to reach room temperature and stirred again for 1 hour. For working up, 1.5 l of methylene chloride were added, water was added with external cooling and stirring and the phases were separated. The organic phase was washed with 2N sodium hydroxide solution and then with saturated sodium chloride solution, dried over sodium sulfate and evaporated down. This procedure gave 40 g of 3-(4-carboxymethylphenyl)-4-dimethoxy-1-(5,6,7,8-tetrahydro- 5,5,8,8-tetramethyl-2-naphthalenyl)-butan-1-one as a crude oily product, which was further reacted without additional purification. The structure was determined by H-NMR spectroscopy.

4-(4-Carbomethoxyphenyl)-2-(5,6,7,8-tetrahydro-5,5,
8,8-tetramethyl- 2-naphthalenyl)-furan:

10 g (22 millimoles) of 3-(4-carbomethoxyphenyl)-4-dimethoxy-1-(5,6,7,8-tetrahydro-5,5,8,8-tetramethyl-2-naphthalenyl)-butan- 1-one in 50 g of concentrated sulfuric acid was stirred for 12 hours at 25° C. Thereafter, the reaction mixture was poured onto ice/water and the precipitate which had separated out was filtered off under suction. Drying and recrystallization from n-heptane gave 3.8 g of the title compound of melting point 109°–111° C.

EXAMPLE 2

4-(4-Carbomethoxyphenyl)-2-(5,6,7,8-tetrahydro-5,5,
8,8-tetramethyl- 2-naphthalenyl)-thiophene:

5.5 g (12 millimoles) of 3-(4-carbomethoxyphenyl)-4-dimethoxy-1-(5,6,7,8-tetrahydro-5,5,8,8-tetramethyl-2-naphthalenyl)-butan-1-one (for preparation see Example 1) and 2.7 g of tetraphosphorus decasulfide in 100 ml of xylene were refluxed for 2 hours. Thereafter, the solvent was distilled off and the residue was purified by column chromatography (silica gel; 1:1 methylene chloride/n-heptane). 1.4 g of the title compound of melting point 108°–110° C. were obtained in this manner.

EXAMPLE 3

4-(4-Carbomethoxyphenyl)-2-(5,6,7,8-tetrahydro-5,5,
8,8-tetramethyl- 2-naphthalenyl)-pyrrole 4.0 g (9 millimoles) of 3-(4-carbomethoxyphenyl)-4-dimethoxy-1-(5,6,7,8-tetrahydro-5,5,8,8-tetramethyl-2-naphthalenyl)-butan- 1-one (for preparation see Example 1) and 3.4 g (44 millimoles) of ammonium acetate in 100 ml of acetic acid was refluxed for 2 hours. The mixture was cooled and then poured onto water and the resulting precipitate was filtered off under suction, dried and recrystallized from n-heptane to give 2.3 g of the title compound of melting point 174°–175° C.

EXAMPLE 4

2-(5,6,7,8-Tetrahydro-5,5,8,8-tetramethyl-2-
naphthalenyl)- 4-(4-tolyl)-furan 1-(5,6,7,8-tetrahydro-5,5,8,8-tetramethyl-2-
naphthalenyl)- 3-(4-tolyl)-prop-2-en-1-one:

10 g of 50% strength sodium hydroxide solution were added dropwise to a solution of 50 g (0.22 mole) of 6-acetyl-1,2,3,4-tetrahydro-1,1,4,4-tetramethylnaphthalene and 26.1 g (0.22 mole) of 4-tolylaldehyde in 250 ml of methanol. The mixture was stirred overnight, after which it was poured onto ice/water and left to stand for several hours. The precipitated crystals were filtered off under suction and dried to give 70 g of 1-( 5,6,7,8-tetrahydro-5,5,8,8-tetramethyl-2-naphthalenyl)- 3-(4-tolyl)-prop-2-en-1-one of melting point 153°–154° C.

4-Dimethoxy-1-(5,6,7,8-tetrahydro-5,5,8,8-tetramethyl-
2-naphthalenyl)-3-(4-tolyl)-butan-1-one:

70 g (90 millimoles) of 1-(5,6,7,8-tetrahydro- 5,5,8,8-tetramethyl-2-naphthalenyl)-(3-(4-tolyl)-prop-2-en- 1-one were converted similarly to Example 1 into 68 g of 4-dimethoxy-1-(5,6,7,8-tetrahydro-5,5,8,8-tetramethyl-2-naphthalenyl)-3-(4-tolyl)-butan-1-one in the form of an oil, which was further reacted without purification. The structure was determined by H-NMR spectroscopy.

2-(5,6,7,8-Tetrahydro-5,5,8,8-tetramethyl-2-
naphthalenyl)- 4-(4-tolyl)-furan:

4.2 g (11 millimoles) of 4-dimethoxy-1-(5,6,7,8-tetrahydro- 5,5,8,8-tetramethyl-2-naphthalenyl)-3-(4-tolyl)-butan-1-one were converted similarly to Example 1 and the product purified by column chromatography (silica gel, methylene chlorine) to give 2.2 g of the title compound of melting point 155°–157° C. (from isopropanol).

EXAMPLE 5

2-(5,6,7,8-Tetrahydro-5,5,8,8-tetramethyl-2-
naphthalenyl)- 4-(4-tolyl)-thiophene 10 g (25 millimoles) of 4-dimethoxy-1-(5,6,7,8-tetrahydro- 5,5,8,8-tetramethyl-2-naphthalenyl)-(3-(4-tolyl)-butan-1-one (for preparation see Example 4) were converted similarly to Example 2 and the product was purified by column chromatography (silica gel; methylene chloride) and recrystallization from n-heptane to give 3.5 g of the title compound of melting point 135°–136° C.

EXAMPLE 6

2-(5,6,7,8-Tetrahydro-5,5,8,8-tetramethyl-2-
naphthalenyl)- 4-(4-tolyl)-pyrrole 5.0 g (12 millimoles) of 4-dimethoxy-1-(5,6,7,8-tetrahydro- 5,5,8,8-tetramethyl-2-naphthalenyl)-(3-(4-tolyl)-butan-1-one (for preparation see Example 4) were converted similarly to Example 1 into 2.1 g of the title compound of melting point 190°–192° C.

EXAMPLE 7

2-(4-Carbomethoxyphenyl)-5-(5,6,7,8-tetrahydro-5,5,
8,8-tetramethyl- 2-naphthalenyl)-furan A solution of 86.4 g (0.4 mole) of 5,6,7,8-tetrahydro-5,5,8,8-tetramethyl-2-naphthaldehyde in 480 ml of tetrahydrofuran was added dropwise at 0° C. to 310 ml (0.48 mole) of a 1.55 molar solution of vinylmagnesium chloride in tetrahydrofuran. Stirring was continued for 10 minutes, after which 60 g (0.4 mole) of acetic anhydride were added dropwise, once again at 0° C. Stirring was continued for 15 minutes, after which saturated sodium chloride solution was added carefully. The mixture was extracted twice with ether, and the organic extracts were washed with water and saturated sodium carbonate solution, dried over sodium sulfate and evaporated down. 100.7 g of 1-O-acetyl-1-(5,6,7,8-tetrahydro-5,5,8,8-tetramethyl- 2-naphthalenyl)-prop-2-en-1-ol remained as an oil.

300 g of 10% strength aqueous sodium hypochlorite solution were added dropwise at 0° C. to a solution of 120 g (0.42 mole) of the above product and 75 g (0.42 mole) of methyl 4-(hydroximino)-methylbenzoate in 500 ml methylene chloride. The mixture was stirred overnight. Thereafter, a further 500 ml of methylene chloride were added, the phases were separated and the aqueous phase was extracted with further methylene chloride. The combined organic phases were washed with water, dried over sodium sulfate and evaporated down. The residue (179.5 g) was taken up in 1.7 l of tetrahydrofuran. 40 ml of 30% strength methanolic sodium methylate solution were added to this solution and the mixture was stirred overnight. The tetrahydrofuran was substantially removed in a rotary evaporator and the remaining oil was taken up in ether. The ether solution was washed twice with water, dried over sodium sulfate and evaporated down.

The residue (118 mg), in a mixture of 1000 ml of tetrahydrofuran, 170 ml of glacial acetic acid and 90 ml of water, was hydrogenated in an autoclave at room temperature using 40 g of Raney nickel under a hydrogen pressure of 50 bar. The reaction mixture was then filtered over Celite to remove the catalyst and the filtrate was evaporated down. The residue (150 g), in a mixture of 750 ml of methylene chloride and 750 ml of 10% strength hydrochloric acid, was stirred for 3 hours at room temperature. Thereafter, the phases were separated and the organic phase was dried over sodium sulfate and evaporated down. The residue was extracted with n-heptane while hot and the n-heptane extract was evaporated down. The remaining oil was crystallized from methanol, and 24.2 g of the title compound of melting point 141°–142° C. were obtained in this manner.

EXAMPLE 8

2-[(4-Hydroxymethyl)-phenyl]-5-(5,6,7,8-tetrahydro-5,5,8,8-tetramethyl-2-naphthalenyl)-furan 3 g (7.7 millimoles) of 2-(4-carbomethoxyphenyl)- 5-(5,6,7,8-tetrahydro-5,5,8,8-tetramethyl-2-naphthalenyl)-furan (Example 7), 1.22 g of lithium chloride and 1.08 g of sodium borohydride in a mixture of 10 ml of tetrahydrofuran and 20 ml of ethanol was stirred overnight at room temperature. Thereafter, ice was added, the pH was brought to 4 with 10% strength citric acid and the tetrahydrofuran was removed in a rotary evaporator. The residue was extracted with methylene chloride. The organic phase was dried with sodium sulfate and evaporated down. Recrystallization from n-heptane gave 1.4 g of the title compound of melting point 124°–125° C.

EXAMPLE 9

2-(4-Carbomethoxyphenyl)-5-(5,6,7,8-tetrahydro-5,5,8,8-tetramethyl- 2-naphthalenyl)-thiophene 6-(3-Chloropropionyl)-1,2,3,4-tetrahydro-1,1,4,4-tetramethylnaphthalene:

73.5 g (0.55 mole) of anhydrous aluminum chloride were added a little at a time, at 0°–5° C., to a solution of 70 g (0.55 mole) of 3-chloropropionyl chloride in 200 ml of methylene chloride, after which a solution of 94 g (0.5 mole) of 1,2,3,4-tetrahydro-1,1,4,4-tetramethylnaphthalene in 200 ml of methylene chloride was added dropwise at the same temperature. The mixture was stirred overnight at room temperature, poured onto 1 l of ice/water and extracted with 3 times 300 ml of methylene chloride. The combined organic phases were washed with saturated sodium bicarbonate solution and water, dried over magnesium sulfate and evaporated down. 138 g of 6-( 3-chloropropionyl)-1,2,3,4-tetrahydro-1,1,4,4-tetramethylnaphthalene remained as an oil. The structure was determined by H-NMR spectroscopy.

1-(4-Carbomethoxyphenyl)-4-(5,6,7,8-tetrahydro-5,5,8,8-tetramethyl-2-naphthalenyl)-butane-1,4-dione 5.6 g (0.02 mole) of 6-(3-chloropropionyl)- 1,2,3,4-tetrahydro-1,1,4,4-tetramethylnapthalene and 3.3 ml (0.024 mole) of triethylamine in 30 ml of dimethylformamide were stirred for 1 hour at room temperature. Thereafter, a solution of 3.6 g (0.025 mole) of methyl 4-formylbenzoate and 1 g of 3-benzyl-5-(2-hydroxyethyl)-4-methylthiazolium chloride in 10 ml of dimethylformamide was added dropwise. Stirring was continued for 1 hour, after which the mixture was poured onto ice/water and extracted twice with ethyl acetate, and the combined organic extracts were washed several times with water, dried over magnesium sulfate and evaporated down. 3.7 g of 1-(4-carbomethoxyphenyl)-4-(5,6,7,8-tetrahydro- 5,5,8,8-tetramethyl-2-naphthalenyl)-butane-1,4-dione of melting point 139°–141° C. were obtained from the residue (6.4 g) after recrystallization from ethanol.

2-(4-Carbomethoxyphenyl)-5-(5,6,7,8-tetrahydro-5,5,8,8-tetramethyl- 2-naphthalenyl)-thiophene:

12.1 g (30 millimoles) of 1-(4-carbomethoxyphenyl)-4-(5,6,7,8-tetrahydro-5,5,8,8-tetramethyl-2-naphthalenyl)-butane- 1,4-dione and 13.4 g (30 millimoles) of tetraphosphorus decasulide in 150ml of o-xylene were heated for 10 minutes at 80° C. under nitrogen. After cooling, the mixture was diluted with ethyl acetate and filtered, and the filtrate was washed with 4 times 100 ml of water, dried over sodium sulfate and evaporated down. The residue was purified by column chromatography (silica gel; n-heptane plus increasing amounts of ethyl acetate). Recrystallization of this crude product from ethanol gave 8.5 g of the title compound of melting point 126°–129° C.

EXAMPLE 10

2-(4-Carbomethoxyphenyl)-5-(5,6,7,8-tetrahydro-5,5,8,8-tetramethyl- 2-naphthalenyl)-pyrrole 8.0 g (20 millimoles) of 1-(4-carbomethoxyphenyl)- 4-(5,6,7,8-tetrahydro-5,5,8,8-tetramethyl-2-naphthalenyl)-butane- 1,4-dione (for preparation see Example 9) and 5.5 g (0.1 mole) of ammonium chloride in 150 ml of dry dimethylformamide were heated for 6 hours at 150° C. After cooling, the mixture was poured onto water and the precipitated crystals were filtered off under suction, washed several times with water and dried in a stream of nitrogen. Purification by column chromatography (silica gel; n-heptane plus increasing amounts of ethyl acetate) and recrystallization from ethanol gave 3.6 g of the title compound of melting point 176°–179° C.

EXAMPLE 11

2-(4-Carbomethoxyphenyl)-1-methyl-5-(5,6,7,8-tetrahydro-
5,5,8,8-tetramethyl-2-naphthalenyl)-pyrrole 8.0 g (20 millimoles) of 1-(4-carbomethoxyphenyl)- 4-(5,
6,7,8-tetrahydro-5,5,8,8-tetramethyl-2-naphthalenyl)-butane- 1,4-dione (for preparation see Example 9) and 6.7 g
(0.1 mole) of methylammonium chloride were converted
similarly to Example 10 and the product was recrystallized
from methanol to give 5.5 g of the title compound of melting
point 104°–105° C.

EXAMPLE 12

3-(4-Carbomethoxyphenyl)-5-(5,6,7,8-tetrahydro-
5,5,8,8-tetramethyl- 2-naphthalenyl)-pyrazole 1-(4-Carbomethoxyphenyl)-3-(5,6,7,8-tetrahydro-
5,5,8,8-tetramethyl-
2-naphthalenyl)-propane-1,3-dione:

A solution of 19.4 g (0.1 mole) of dimethyl terephthalate
and 23 g (0.1 mole) of 6-acetyl-1,2,3,4-tetrahydro- 1,1,4,4-
tetramethylnaphthalene in a mixture of 80 ml of toluene and
20 ml of dimethoxyethane was added dropwise at 100° C. to
a suspension of 6.3 g (0.15 mole) of sodium hydride in 21
ml of toluene under nitrogen. The reaction mixture was
refluxed with stirring for 5 hours and then cooled, after
which 50 ml of water were added and the mixture was
acidified with semiconcentrated hydrochloric acid, poured
onto 500 ml of water and extracted with chloroform. The
product which had already precipitated was filtered off under
suction, and the chloroform phase was dried over sodium
sulfate and evaporated down. The residue and the crude
product filtered off under suction beforehand were combined
and were extracted several times with hot methanol. After
the remaining crystals had been dried, 22.1 g of 1-(4-
carbomethoxyphenyl)- 3-(5,6,7,8-tetrahydro-5,5,8,8-tetramethyl- 2-naphthalenyl)-propane-1,3-dione of melting point
128° C. were obtained.

3-(4-Carbomethoxyphenyl)-5-(5,6,7,8-tetrahydro-
5,5,8,8-tetramethyl- 2-naphthalenyl)-pyrazole:

6.0 g (15 millimoles) of 1-(4-carbomethoxyphenyl)- 3-(5,
6,7,8-tetrahydroxy-5,5,8,8-tetramethyl-2-naphthalenyl)-
propane- 1,3-dione and 1.2 g of hydrazine hydrate in a
mixture of 30 ml of tetrahydrofuran and 20 ml of methanol
were refluxed for 4 hours. The mixture was allowed to cool
and poured onto water, and the precipitate was filtered off
under suction. Recrystallization from methanol gave 3.8 g of
the title compound of melting point 155°–156° C.

EXAMPLE 13

3-(4-Carbomethoxyphenyl)-5-(2,3-dihydro-1,1,2,3,3-
pentamethyl- 5(1H)-indenyl)-pyrazole In a procedure similar to that of Example 12, 23 g (0.1
mole) of 5-acetyl-2,3-dihydro-1,1,2,3,3-pentamethyl-( 1H)-
indene gave 18.1 g of 1-(4-carbomethoxyphenyl)- 3-(2,3-
dihydro-1,1,2,3,3-pentamethyl-5(1H)-indenyl)-propane-
1,3-dione and 5 g (13 millimoles) of the latter gave 1.5 g of
the title compound.

EXAMPLE 14

3-(4-Carbomethoxyphenyl)-5-(5,6,7,8-tetrahydro-
3,8,8-trimethyl- 2-naphthalenyl)-pyrazole In a procedure similar to that of Example 12, 10 g (46
millimoles) of 7-acetyl-1,2,3,4-tetrahydro-1,1,6-trimethylnaphthalene gave 4.8 g of 1-(4-carbomethoxyphenyl)- 3-(5,
6,7,8-tetrahydro-3,8,8-trimethylnaphthalenyl)-propane-
1,3-dione of melting point 91°–92° C., and 2.9 g (7.6
millimoles) of the latter gave 2.8 g of the title compound of
melting point 92°–93° C.

EXAMPLE 15

1-(4-Carboxyphenyl)-4-(5,6,7,8-tetrahydro-
5,5,8,8-tetramethyl- 2-naphthalenyl)-pyrazole 11.7 g (0.15 mole) of potassium tert-butylate were added
at 0°–10° C. to a solution of 23.0 g (0.105 mole) of
trimethylsulfoxonium iodide in 100 ml of dried dimethylformamide. The mixture was allowed to reach room temperature and a solution of 25.4 g (0.088 mole) of
6-dimethoxyacetyl- 1,2,3,4-tetrahydro-1,1,4,4-tetramethylnaphthalene in 25 ml of dimethylformamide was added
dropwise. Stirring was continued for 1 hour and the mixture
was extracted with water/ether. The ether phase was washed
with water, dried over sodium sulfate and evaporated down.
23.5 g of crude 2-dimethoxymethyl-2-( 5,6,7,8-tetrahydro-
5,5,8,8-tetramethyl-2-naphthalenyl)oxirane remained,
which was used without additional purification.

13.0 g (43 millimoles) of this oxirane and 65 ml of glacial
acetic acid were refluxed for 5 hours. Thereafter, 6.5 g (43
millimoles) of 4-hydrazinobenzoic acid were added and the
refluxed mixture was stirred until the reaction was complete
(check by thin-layer chromatography). The mixture was
poured onto water and extracted with ether. The organic
phase was washed twice with saturated sodium bicarbonate
solution, dried over sodium bicarbonate/sodium sulfate and
evaporated down. After recrystallization from n-heptane and
again from isopropanol, the oily residue gave 2.1 g of the
title compound of melting point 229°–232° C.

EXAMPLE 16

1-(4-Carboxyphenyl)-3-(5,6,7,8-tetrahydro-
5,5,8,8-tetramethyl- 2-naphthalenyl)-2-pyrazoline 2.8 g (10 millimoles) of 6-3-chloropropionyl)- 1,2,3,4-
tetrahydro-1,1,4,4-tetramethylnaphthalene (for preparation
see Example 9) and 1.5 g (10 millimoles) of 4-hydrazinobenzoic acid in 40 ml of dimethylformamide was stirred
until the reaction was complete (check by thin-layer chromatography). The mixture was poured onto water and the
resulting crystals were filtered off under suction and washed
with water and ethanol. Drying gave 2.2 g of the title
compound of melting point 276°–278° C.

EXAMPLE 17

1-(4-Carboxyphenyl)-3-(5,6,7,8-tetrahydro-
5,5,8,8-tetramethyl-
2-naphthalenyl)-Δ2-pyrazolin-5-one Ethyl
3-oxo-3-(5,6,7,8-tetrahydro-5,5,8,8-tetramethyl-2-
naphthalenyl)-propionate:

15 g (0.23 mole) of zinc powder and 1.5 g (8.3 millimoles)
of copper(II) acetate monohydrate in 50 ml of glacial acetic acid were stirred for 30 minutes while cooling with ice. The mixture was then stirred with 50 ml of dry ether, and the solid was filtered off under suction and washed twice with dry ether and once with dry tetrahydrofuran. The solution of 21.6 g (0.1 mole) of 5,6,7,8-tetrahydro-5,5,8,8-tetramethyl-2-naphthaldehyde and 21.0 g (0.125 mole) of ethyl bromoacetate in 500 ml of dry tetrahydrofuran was added dropwise to a suspension of a zinc/copper product pair prepared in this manner, the reaction reaching the reflux temperature. The refluxing mixture was stirred for a further 75 minutes, cooled, acidified with 5N sulfuric acid and filtered. The filtrate was extracted with ether and the organic phase was washed with water, dried over sodium sulfate and evaporated down. The residue (27.8 g) was dissolved in 100 ml of acetone, and a solution of 12.0 g (0.12 mole) of chromium(VI) oxide in 36.8 ml of water and 12.9 ml of concentrated sulfuric acid was added dropwise at 10° C. Stirring was continued for 30 minutes at 10° C., after which the mixture was poured onto ice/water and was extracted with ether. The organic phase was washed twice with water, dried over sodium sulfate and evaporated down. Distillation hydrochloric acid, and the precipitate which had separated out was filtered off under suction and dried to give 5.1 g of 5,6,7,8-tetrahydro-3-methoxy- 5,5,8,8-tetramethyl-2-naphthaldoxime of melting point 182°–183° C.

17.2 g of a 10% strength aqueous sodium hypochlorite solution were added dropwise at 10°–15° C. to a solution of 5.0 g (19 millimoles) of 5,6,7,8-tetrahydro- 3-methoxy-5,5,8,8-tetramethyl-2-naphthaldoxime and 2.4 g (19 millimoles) of 4-ethynylbenzonitrile. The mixture was stirred for 1.5 hours at room temperature. Thereafter, the reaction mixture was poured onto water, the phases were separated and the aqueous phase was extracted again with methylene chloride. The combined organic extracts were washed with sodium bisulfite solution, dried over sodium sulfate and evaporated down. The residue was digested in hot methanol, the mixture was allowed to cool and the crystals were filtered off under suction and dried to give 5.4 g of the title compound of melting point 202°–203° C.

EXAMPLES 19–24

The isoxazoles shown in Table I were prepared similarly to Example 18.

TABLE 1

[Structure: A substituted naphthalenyl-isoxazole with phenyl-CN group, bearing substituents R¹, R², R³, R⁴, R⁵ and ring A]

| Example | A | $R^1$ | $R^2$ | $R^3$ | $R^4$ | $R^5$ | H-NMR (δ in ppm, Isoxazole-H) |
|---|---|---|---|---|---|---|---|
| 18 | —CH$_2$CH$_2$— | CH$_3$ | CH$_3$ | H | OCH$_3$ | H | 7.16 |
| 19 | —CH$_2$CH$_2$— | CH$_3$ | CH$_3$ | H | H | H | 6.9 |
| 20 | —CH$_2$—CH$_2$— | CH$_3$ | CH$_3$ | H | CH$_3$ | H | 6.84 |
| 21 | —CH$_2$—CH$_2$— | CH$_3$ | CH$_3$ | OCH$_3$ | OCH$_3$ | H | 6.86 |
| 22 | —CH$_2$—CH$_2$ | CH$_3$ | CH$_3$ | OCH$_3$ | H | OCH$_3$ | 7.18 |
| 23 | —CH$_2$—CH$_2$ | CH$_3$ | CH$_3$ | O-n-C$_3$H$_7$ | CH$_3$ | H | 6.82 |
| 24 | —CH$_2$—CH$_2$ | CH$_3$ | CH$_3$ | H | F | H | 7.08 | of the residue gave 9.0 g of ethyl 3-oxo- 3-(5,6,7,8-tetrahydro-5,5,8,8-tetramethyl-2-naphthalenyl)-propionate of boiling point 150°–152° C./0.4 mbar.

1-(4-Carboxyphenyl)-3-(5,6,7,8-tetrahydro- 5,5,8,8-tetramethyl-2-naphthalenyl)-Δ2-pyrazolin-5-one 1.5 g (5 millimoles) of ethyl 3-oxo-3-(5,6,7,8-tetrahydro-5,5,8,8-tetramethyl-2-naphthalenyl)-propionate and 0.75 g (5 millimoles) of 4-hydrazinobenzoic acid in 40 ml of ethanol was stirred for 4 hours at 40° C. The mixture was poured onto water and was extracted with ether. The ether phase was washed twice with water, dried over sodium sulfate and evaporated down. Recrystallization of the solid residue from methanol/methylene chloride gave 0.6 g of the title compound of melting point 275°–277° C.

EXAMPLE 18

5-(4-Cyanophenyl)-3-(5,6,7,8-tetrahydro-3-methoxy-5,5,8,8-tetramethyl-2-naphthalenyl)-isoxazole 5 g (20 millimoles) of 5,6,7,8-tetrahydro-3-methoxy- 5,5,8,8-tetramethyl-2-naphthaldehyde and 2.1 g (30 millimoles) of hydroxylammonium chloride in 32.5 ml of dry pyridine were refluxed for 2 hours. The mixture was then allowed to cool, poured onto water and acidified with concentrated

EXAMPLE 25

5-(4-Formylphenyl)-3-(5,6,7,8-tetrahydro-5,5,8,8-tetramethyl- 2-naphthalenyl)-isoxazole 8.8 ml of a 1M solution of diisobutylaluminum hydride in n-hexane were added dropwise at room temperature to a solution of 1.5 g (4.2 millimoles) of 5-(4-cyanophenyl)-3-(5,6,7,8-tetrahydro-5,5,8,8-tetramethyl-2-naphthalenyl)-isoxazole (Example 19) in 20 ml of dry ether under nitrogen, and the mixture was stirred for 1 hour. Thereafter, 2 ml of saturated tartaric acid solution were added, a little magnesium sulfate was introduced, the mixture was stirred for 15 minutes and filtered and the filtrate was evaporated down. Recrystallization of the residue from isopropanol gave 0.6 g of the title compound of melting point 179°–180° C.

EXAMPLE 26

5-[4-(Aminomethyl)-phenyl]-3-(5,6,7,8-tetrahydro-5,5,8,8-tetramethyl- 2-naphthalenyl)-isoxazole 0.95 g (2.7 millimoles) of 5-(4-cyanophenol)-3-( 5,6,7,8-tetrahydro-5,5,8,8-tetramethyl-2-naphthalenyl)-isoxazole (Example 19) were added a little at a time, at room temperature, to a suspension of 0.28 g (7.4 millimoles) of lithium aluminum hydride in 30 ml of dry ether. The mixture was then refluxed for 3 hours and cooled, after which hydrolysis was carried out carefully with water, the phases were separated, the aqueous phase was extracted again with ether and the combined organic extracts were dried over sodium sulfate and evaporated down. 0.9 g of the title compound of melting point 138°– 143° C. remained as the residue.

EXAMPLE 27

2-(4-Carbomethoxyphenyl)-4-(5,6,7,8-tetrahydro-5,5,8,8-tetramethyl- 2-naphthalenyl)-oxazole 15 g (65 millimoles) of 6-acetyl-1,2,3,4-tetrahydro- 1,1, 4,4-tetramethylnaphthalene and 6.5 g (91 millimoles) of hydroxylammonium chloride in 100 ml of pyridine were heated for 1 hour at 80° C. After cooling, the mixture was poured onto water and acidified with 2N hydrochloric acid. The precipitated crystals were filtered off under suction, washed with water and dried. 16 g of 6-[1-hydroximinoethyl]-1,2,3,4-tetrahydro-1,1,4,4-tetramethylnaphthalene were obtained in this manner. 5 g (20 millimoles) thereof and 5 g (20 millimoles) of terephthalic monomethyl ester chloride were combined and were stirred for 6 hours at 120° C. After cooling, the solidified material was dissolved with about 60 ml of methanol. The supernatant methanol phase was decanted and the solid residue was recrystallized twice from chloroform/methanol. 2.5 g of the title compound of melting point 207°–208° C. were obtained in this manner.

EXAMPLE 28

2-(4-Carbomethoxyphenyl)-5-(5,6,7,8-tetrahydro-5,5,8,8-tetramethyl- 2-naphthalenyl)-oxazole 6-Chloroacetyl-1,2,3,4-tetrahydro-1,1,4,4-tetramethylnaphthalene:

A solution of 68 g (0.36 mole) of 1,2,3,4-tetrahydro-1,1,4,4-tetramethylnaphthalene in 200 ml of methylene chloride was added dropwise at 0°–5° C. to a solution of 72 g (0.55 mole) of anhydrous aluminum chloride and 40.7 g (0.36 mole) of chloroacetyl chloride in 270 ml of dry methylene chloride. Stirring was then carried out overnight at room temperature. The mixture was poured onto ice/water and extracted with methylene chloride, and the organic phase was washed several times with water, dried over sodium sulfate and evaporated down. 92.2 g of 6-chloroacetyl-1,2,3,4-tetrahydro-1,1,4,4-tetramethylnaphthalene remained as an oil. The structure was determined by H-NMR spectroscopy.

6-Azidoacetyl-1,2,3-tetrahydro-1,1,4,4-tetramethylnaphthalene:

8.9 g (136 millimoles) of sodium azide were introduced a little at a time into a solution of 30 g (113 millimoles) of 6-chloroacetyl-1,2,3,4-tetrahydro- 1,1,4,4-tetramethylnaphthalene in 120 ml of dimethyl sulfoxide. The mixture was stirred for 1 hour at room temperature and then poured onto ice/water and extracted with ethyl acetate, and the organic phase was washed with water, dried-over sodium sulfate and evaporated down. 32.4 g of crude 6-azidoacetyl-1,2,3,4-tetrahydro-1,1,4,4-tetramethylnaphthalene remained. The structure was determined by H-NMR spectroscopy.

6-Aminoacetyl-1,2,3,4-tetrahydro-1,1,4,4-tetramethylnaphthalene hydrochloride:

16.2 g (63.5 millimoles) of 6-aminoacetyl- 1,2,3,4-tetrahydro-1,1,4,4-tetramethylnaphthalene in 250 ml of methanol and 59 ml of 2N hydrochloric acid were hydrogenated with 2.9 g of 10% strength palladium on active carbon at room temperature and under atmospheric pressure. The reaction mixture was filtered over Celite and the filtrate was evaporated down. The residue was stirred with ether and a few drops Of methanol and the precipitated crystals were filtered off under suction. After drying, 5.8 g of 6-aminoacetyl-1,2,3,4-tetrahydro- 1,1,4,4-tetramethylnaphthalene hydrochloride remained. The structure was determined by H-NMR spectroscopy.

2-N-(4-Carbomethoxybenzoyl)-amino-1-(5,6,7,8-tetrahydro-5,5,8,8-tetramethyl-2-naphthalenyl)-ethanone:

5 g of triethylamine were added dropwise at from 0° to 10° C. to a solution of 5.6 g (20 millimoles) of 6-aminoacetyl- 1,2,3,4-tetrahydro-1,1,4,4-tetramethylnaphthalene hydrochloride and 4.0 g (20 millimoles) of terephthalic monomethyl ester chloride in 40 ml of dimethylformamide. The reaction mixture was stirred for 15 minutes, allowed to reach room temperature, poured onto water and extracted three times with ether. The combined organic extracts were washed with water, dried over sodium sulfate and evaporated down. After recrystallization from n-heptane/toluene, the residue gave 4.4 g of 2-N- 4-(carbomethoxybenzoyl)-amino-1-(5,6,7,8-tetrahydro-5,5,8,8-tetramethyl-2-naphthalenyl)-ethanone of melting point 126°–128° C.

2-(4-Carbomethoxyphenyl)-5-(5,6,7,8-tetrahydro-5,5,8,8-tetramethyl- 2-naphthalenyl)-oxazole:

3 g (7.4 millimoles) of 2-N-(4-carbomethoxybenzoyl)-amino- 1-(5,6,7,8-tetrahydro-5,5,8,8-tetramethyl- 2-naphthalenyl)-ethanone in 20 ml of concentrated sulfuric acid were stirred for 20 minutes at room temperature. The mixture was poured onto ice water and stirred for 15 minutes, and the crystals were filtered off under suction and dried to give 2.8 g of the title compound of melting point 153°–155° C.

EXAMPLE 29

3-(4-Carbethoxyphenyl)-5-(5,6,7,8-tetrahydro-5,5,8,8-tetramethyl- 2-naphthalenyl)-oxazolidine (5,6,7,8-Tetrahydro-5,5,8,8-tetramethyl-2-naphthalenyl)oxirane:

33 g (0.15 mole) of trimethylsulfoxonium iodide were added at room temperature to a solution of 17 g (0.15 mole) of potassium tert-butylate in 150 ml of dried dimethyl sulfoxide. The mixture was stirred for 0.5 hour, after which a solution of 32.5 g (0.15 mole) of 5,6,7,8-tetrahydro-5,5,8,8-tetramethyl-2-naphthaldehyde in 100 ml of tetrahydrofuran was added dropwise. Stirring was continued for 1 hour, after which the mixture was poured onto water and extracted with ether. The organic phase was washed with water, dried over magnesium sulfate and evaporated down. 31.3 g of (5,6,7,8-tetrahydro- 5,5,8,8-tetramethyl-2-naphthalenyl)-oxirane remained. The structure was determined by H-NMR spectroscopy.

N-(4-Carbethoxyphenyl)-1-(5,6,7,8-tetrahydro-
5,5,8,8-tetramethyl-
2-naphthalenyl)-2-aminoethanol:

26 g (110 millimoles) of (5,6,7,8-tetrahydro- 5,5,8,8-tetramethyl-2-naphthalenyl)-oxirane, 15 g (90 millimoles) of ethyl 4-aminobenzoate, 135 g of basic alumina and 450 ml of toluene were refluxed for 2 hours. The solid was then filtered off and the filtrate was evaporated down. After recrystallization from n-heptane with a little ethyl acetate, the residue gave 11.0 g of N-(4-carbethoxyphenyl)-1-(5,6,7,8-tetrahydro-5,5,8,8-tetramethyl- 2-naphthalenyl)-2-aminoethanol. The structure was determined by H-NMR spectroscopy.

3-(4-Carbethoxyphenyl)-5-(5,6,7,8-tetrahydro-5,5,8,8-tetramethyl- 2-naphthalenyl)-oxazolidine:

1.58 g (4 millimoles) of N-(4-carbethoxyphenyl)- 1-(5,6,7,8-tetrahydro-5,5,8,8-tetramethyl-2-naphthalenyl)- 2-aminoethanol were stirred with 20 ml of 1N sodium hydrogen phosphite solution and 2 ml (20 millimoles) of formalin solution in 20 ml of dioxane for 1 hour at 60° C. The mixture was then poured onto water and extracted with ether, and the organic phase was washed with 2N sodium hydroxide solution and water, dried over magnesium sulfate and evaporated down. Recrystallization from methanol gave 1.0 g of the title compound, $R_F$=0.51 (thin layer chromatography, silica gel; 7:1 n-heptane/ethyl acetate).

EXAMPLE 30

2-(4-Carbomethoxyphenyl)-4-(5,6,7,8-tetrahydro-
5,5,8,8-tetramethyl- 2-naphthalenyl)-thiazole:

130 g (1.7 moles) of thioacetic acid, 50 g (0.3 mole) of methyl 4-cyanobenzoate and 12 ml of glacial acetic acid were stirred for 2 hours at 80° C. The mixture was allowed to cool, 200 ml of 1:1 isopropanol/water was added, the mixture was stirred for a short time and the crystals formed were filtered off under suction. 45.5 g of 4-carbomethoxybenzothiamide of melting point 188°–190° C. were obtained in this manner.

3.2 g (16.5 moles) of 4-carbomethoxybenzothiamide and 4.2 g (16 millimoles) of 6-chloroacetyl-1,2,3,4-tetrahydro-1,1,,4,4-tetramethylnaphthalene (for preparation see Example 28) in 40 ml of isopropanol were refluxed for 1 hour with the addition of 2 drops of pyridine. The mixture was cooled, water was added and the crystals formed were filtered off under suction. Recrystallization from isopropanol and a trace of water gave 3.0 g of the title compound of melting point 138°–140° C.

EXAMPLE 31

4-(4-Carbethoxyphenyl)-2-(5,6,7,8-tetrahydro-
5,5,8,8-tetramethyl- 2-naphthalenyl)-imidazole 2.6 g (10 millmoles) of 6-chloroacetyl-1,2,3,4-tetrahydro-1,1,4,4-tetramethylnaphthalene (for preparation see Example 28), 2.1 g (10 millimoles) of 4-carbethoxybenzamidinium chloride and 5 g of potassium carbonate in 100 ml of dimethylformamide were refluxed for 1 hour. After cooling, the mixture was poured onto water and stirred for 10 minutes, and the precipitate formed was filtered off under suction. Purification by column chromatography (silica gel; 9:1 n-heptane/ethyl acetate) gave 0.3 g of the title compound of melting point 186°–188° C.

EXAMPLE 32

5-(5,6,7,8-tetrahydro-5,5,8,8-tetramethyl-
2-naphthalenyl)- 3-(4-tolyl)-1,2,4-oxadiazole 8.0 g (30 millimoles) of 5,6,7,8-tetrahydro- 5,5,8,8-tetramethyl-2-naphthoyl chloride and 4.5 g (30 millimoles) of 4-methylbenzamidoxime in 250 ml of dioxane were refluxed for 1 hour. 1 ml of boron trifluoride dietherate were added and refluxing was continued for a further 4 hours. The mixture was allowed to cool, poured onto ice/water and extracted with methylene chloride. The organic phase was washed several times with water, dried over magnesium sulfate and evaporated down. The oily residue was purified by column chromatography (silica gel; n-heptane+0.5% of ethyl acetate), and the crude product obtained from the first fractions was recrystallized from methanol to give 3.2 g of the title compound of melting point 106°–109° C.

EXAMPLE 33

5-(4-Carbomethoxyphenyl)-3-(5,6,7,8-tetrahydro-
5,5,8,8-tetramethyl-
2-naphthalenyl)-1,2,4-oxadiazole 7.6 g (0.11 mole) of hydroxylammonium chloride were introduced a little at a time into a boiling solution of 21.6 g (0.1 mole) of 5,6,7,8-tetrahydro- 5,5,8,8-tetramethyl-2-naphthaldehyde in 25 ml of dimethylformamide in such a way that the reaction mixture remained at the boil. The refluxing mixture was stirred for 30 minutes, cooled and then diluted with three times its volume of water and extracted with ether. The organic phase was washed several times with water, dried over magnesium sulfate and evaporated down. 17.2 g of oily 6-cyano-1,2,3,4-tetrahydro-1,1,4,4-tetramethylnaphthalene remained. 15 g (70 millimoles) of this oil, 4.8 g (35 millimoles) of potassium carbonate and 4.9 g (70 millimoles) of hydroxylammonium chloride in 175 ml of ethanol and 35 ml of water were refluxed for 10 hours. After cooling, the solids were filtered off and the filtrate was evaporated down. The residue was extracted with methylene chloride/water and the organic phase was separated off, dried over magnesium sulfate and evaporated down. 17.2 g of 5,6,7,8-tetrahydro-5,5,8,8-tetramethylnaphthalene- 2-carboxamide oxime remained as a solid material, which was further reacted without additional purification.

4.1 g of the title compound of melting point 166°–168° C. (from pentate) were obtained in a similar manner, by the process described in Example 32, from 6.5 g (30 millimoles) of terephthalic monomethyl ester chloride and 7.4 g (30 millimoles) of 5,6,7,8-tetrahydro-5,5,8,8-tetramethylnaphthalene- 2-carboxamide oxime.

EXAMPLE 34

2-(4-Carbamylphenyl)-5-(5,6,7,8-tetrahydro-
5,5,8,8-tetramethyl-
2-naphthalenyl)-1,3,4-oxadiazole N-(4-Cyanobenzoyl)-N'-(5,6,7,8-tetrahydro-
5,5,8,8-tetramethyl- 2-naphthoyl)-hydrazine:

23.2 g (0.1 mole) of 5,6,7,8-tetrahydro-5,5,8,8-tetramethylnaphthalene- 2-carboxylic acid and 18 g (0.15 mole) of thionyl chloride in 75 ml of toluene were heated until hydrogen chloride gas was no longer formed. Thereafter, the mixture was evaporated down, toluene was added several times and the mixture was evaporated down again to remove residual thionyl chloride. The residue was dissolved in 75 ml of isopropanol and added dropwise at from −10° to −15° C. to a solution of 7.4 g (0.23 mole) of hydrazine in 200 ml of isopropanol. The mixture was stirred for 15 minutes at −10° C., 150 ml of water and 50 ml of ether were added and the mixture was stirred again vigorously. The mixture was left to stand overnight, after which the solid was filtered off and the filtrate was extracted with water/ether. The organic phase was washed with water, dried over sodium sulfate and evaporated down. 19.7 g (0.08 mole) of the 5,6,7,8-tetrahydro- 5,5,8,8-tetramethylnaphthalene-2-carboxylic hydrazide remaining as the residue were dissolved in 100 ml of dry tetrahydrofuran. A solution of 13.5 (0.088 mole) of 4-cyanobenzoyl chloride in 100 ml of tetrahydrofuran was added dropwise at 0° C. The stirred reaction mixture was allowed to reach room temperature in the course of 45 minutes. It was poured onto water, and the precipitated solid was filtered off, washed with ethanol and dried to give 16.4 g of N-(4-cyanobenzoyl)-N'-(5,6,7,8-tetrahydro- 5,5,8,8-tetramethyl-2-naphthoyl)-hydrazine of melting point 274°–277° C.

2-(4-Carbamylphenyl)-5-(5,6,7,8-tetrahydro-5,5,8,8-tetramethyl- 2-naphthalenyl)-1,3,4-oxadiazole:

5.8 g (15.5 millimoles) of N-(4-cyanobenzoyl)-N'-(5,6,7, 8-tetrahydro-5,5,8,8-tetramethyl-2-naphthalenyl)-hydrazine and 75 g of polyphosphoric acid were combined and the mixture was stirred for 6 hours at 100° C. Thereafter, it was poured onto ice/water and the precipitated crystals were filtered off under suction. The still moist crystals were recrystallized from isopropanol, and 3.3 g of the title compound of melting point 272°–274° C. were obtained in this manner.

EXAMPLE 35

5-(4-Carbomethoxyphenyl)-3-(5,6,7,8-tetrahydro-5,5,8,8-tetramethyl- 2-naphthalenyl)-pyridazine 8 g (18 millimoles) of 3-(4-carbomethoxyphenyl)-4-dimethoxy-1-(5,6,7,8-tetrahydro-5,5,8,8-tetramethyl-2-naphthalenyl)-butan- 1-one (for preparation see Example 1) and 3.3 g of hydrazine hydrate in 150 ml of acetic acid were refluxed for 1 hour. After cooling, the mixture was poured onto water and brought to pH 5–6 with 2 N sodium hydroxide solution, and the precipitate formed was filtered off under suction and dried. Recrystallization from isopropanol/ n-heptane gave 1.5 of the title compound; H-NMR (CDCl$_3$): δ=8.02 and 9.39 ppm (in each case d, 2H, pyridazine-H).

EXAMPLE 36

3-(4-Carbomethoxyphenyl)-6-(5,6,7,8-tetrahydro-5,5,8,8-tetramethyl- 2-naphthalenyl)-pyridazine 0.3 g (10 millimoles) of 100% pure hydrazine were added dropwise at room temperature to a solution of 4.0 g (10 millimoles) of 1-(4-carbomethoxyphenyl)-4-(5,6,7,8-tetrahydro- 5,5,8,8-tetramethyl-2-naphthalenyl)-butane- 1,4-dione (for preparation see Example 9) in 50 ml of ethanol. The reaction mixture was then refluxed for 20 minutes, cooled and then stirred into water, and the yellow crystals were filtered off under suction and dried in a stream of nitrogen. For aromatization of unoxidized dihydropyridazine, the crude product was stirred with periodic acid in ethanol until checking by thin layer chromatography showed that mainly a pure product was obtained. The product was then diluted with water, rendered basic with 2N sodium hydroxide solution and extracted with methylene chloride. The organic phase was washed with water, dried over magnesium sulfate and evaporated down. 3.1 g of the title compound remained as an oil; H-NMR (CF$_3$COOH):=8.82 and 8.88 ppm (in each case d, 2H, pyridazine-H).

EXAMPLE 37

4-(4-Carbobutoxyphenyl)-2-hydroxy-6-(5,6,7,8-tetrahydro-5,5,8,8-tetramethyl-2-naphthalenyl)-pyrimidine 21 g (0.1 mole) of 6-ethynyl-1,2,3,4-tetrahydro- 1,1,4,4-tetramethylnaphthalene, 16 g (0.1 mole) of methyl 4-formylbenzoate, 9 g (0.15 mole) of urea and 15 ml of concentrated sulfuric acid in 50 ml of n-butanol were refluxed for 4 hours. After cooling, the mixture was poured onto 500 ml of water, 100 ml of ether were added and stirring was carried out for 5 minutes. A solid was precipitated between phases. In a shaking funnel, the aqueous phase was separated off and the residue was again washed with water and then shaken thoroughly with 200 ml of petroleum ether. The precipitate was filtered off under suction and washed with petroleum ether. 6.5 g of the title compound of melting point 267°–277° C. were obtained in this manner.

EXAMPLE 38

1-(4-Carboxyphenyl)-2-mercapto-4-(5,6,7,8-tetrahydro-5,5,8,8-tetramethyl-2-naphthalenyl)-imidazole 2-N-(4-Carboxyphenyl)-amino-1-(5,6,7,8-tetrahydro-5,5,8,8-tetramethyl-2-naphthalenyl)-ethanone 40 g (0.4 mole) of triethylamine were added to a solution of 25 g (0.186 mole) of ethyl 4-aminobenzoate in 70 ml of dimethylformamide while cooling, followed by the dropwise addition of a solution of 41 g (0.4 mole) of 6-chloroacetyl- 1,2,3,4-tetrahydro-1,1,4,4-tetraethylnaphthalene (for preparation see Example 28), likewise with cooling. Stirring was then carried out for 3 hours at room temperature. The reaction mixture was then poured onto water and stirred for 30 minutes in an ice bath, and the resulting precipitate was filtered off under suction, washed with water and dried. Recrystallization from ethanol gave 22.6 g of 2-N-(4-carboxyphenyl)-amino-1-(5,6,7,8-tetrahydro-5,5,8,8-tetramethyl- 2-naphthalenyl)-ethanone of melting point 168°–169° C. 1-(4-Carboxyphenyl)-2-mercapto-4-(5,6,7,8-tetrahydro-5,5,8,8-tetramethyl-2-naphthalenyl)-imidazole 3.6 g (10 millimoles) of 2-N-(4-carboxyphenyl)amino-1-(5,6,7,8-tetrahydro-5,5,8,8-tetramethyl-2-naphthalenyl)-ethanone were suspended in 40 ml of 1N hydrochloric acid. 2 g of potassium thiocyanate were added and the mixture was heated to the reflux temperature. Soon thereafter, a second phase formed; the mixture was allowed to cool to 60° C., 30 ml of isopropanol were added and refluxing was carried out for 9 hours. After the mixture had cooled, the solid was filtered off and washed with water. Recrystallization from methanol/acetone gave 1.3 g of the title compound of melting point 170°–172° C.

EXAMPLE 39–61

Examples 39–61 of Table 2 below were obtained by the following general method:

6 millimoles of ester or nitrile in a mixture of 16 ml of 10N sodium hydroxide solution and 22 ml of ethanol were refluxed for 2 hours. The mixture was cooled, then poured onto water and acidified with concentrated sulfuric acid, and the precipitate formed was filtered off under suction and dried. If necessary, recrystallization was then carried out from a suitable solvent.

TABLE 2

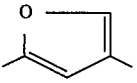

| Example | A | R¹ | R² | R³ | R⁴ | R⁵ | L | from R⁶ = | mp. (°C.) |
|---|---|---|---|---|---|---|---|---|---|
| 39 | —CH₂CH₂— | CH₃ | CH₃ | H | H | H | 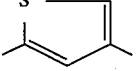 | —COOCH₃ | 215–217 |
| 40 | —CH₂—CH₂— | CH₃ | CH₃ | H | H | H | 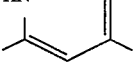 | —COOCH₃ | 235–237 |
| 41 | —CH₂—CH₂— | CH₃ | CH₃ | H | H | H | 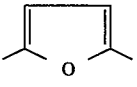 | —COOCH₃ | 266–267 |
| 42 | —CH₂—CH₂— | CH₃ | CH₃ | H | H | H | 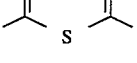 | —COOCH₃ | 261–262 |
| 43 | —CH₂—CH₂— | CH₃ | CH₃ | H | H | H | 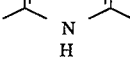 | —COOCH₃ | 281–285 |
| 44 | —CH₂—CH₂— | CH₃ | CH₃ | H | H | H | 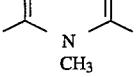 | —COOCH₃ | 269–271 |
| 45 | —CH₂—CH₂— | CH₃ | CH₃ | H | H | H | 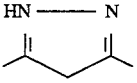 | —COOCH₃ | 217–219 |
| 46 | —CH₂CH₂ | CH₃ | CH₃ | H | H | H | 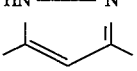 | —COOCH₃ | 289–290 |
| 47 | —CH₂CH₂— | H | H | H | CH₃ | H | 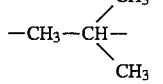 | —COOCH₃ | 300 |
| 48 | —CH₃—CH(CH₃)CH₃ | CH₃ | CH₃ | H | H | H | 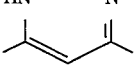 | —COOCH₃ | 300 |
| 49 | —CH₂CH₂— | CH₃ | CH₃ | H | H | H | 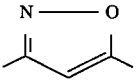 | —CN | 167–168 |
| 50 | —CH₂CH₂— | CH₃ | CH₃ | H | OCH₃ | H | 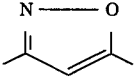 | —CN | 228–229 |
| 51 | —CH₂CH₂— | CH₃ | CH₃ | H | CH₃ | H | 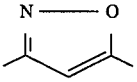 | —CN | 237–238 |

TABLE 2-continued

![structure with A, R¹, R², R³, R⁴, R⁵, L substituents on biphenyl-COOH]

| Example | A | R¹ | R² | R³ | R⁴ | R⁵ | L | from R⁶ = | mp. (°C.) |
|---|---|---|---|---|---|---|---|---|---|
| 52 | —CH₂CH₂— | CH₃ | CH₃ | H | F | H | N—O (C=N, C=C with methyls) | —CN | 250 |
| 53 | —CH₂CH₂— | CH₃ | CH₃ | OCH₃ | H | OCH₃ | N—O | —CN | 208–210 |
| 54 | —CH₂CH₂— | CH₃ | CH₃ | OCH₃ | OCH₃ | H | N—O | —CN | 250–252 |
| 55 | —CH₂CH₂— | CH₃ | CH₃ | O-n-C₃H₇ | CH₃ | H | N—O | —CN | 258–265 |
| 56 | —CH₂CH₂— | CH₃ | CH₃ | H | H | H | O—N (morpholine-like) | —COOC₂H₅ | 258–265 |
| 57 | —CH₂CH₂— | CH₃ | CH₃ | H | H | H | N—N—NH (pyrazole) | —COOCH₃ | |
| 58 | —CH₂CH₂— | CH₃ | CH₃ | H | H | H | N—O with N | —COOCH₃ | 263–265 |
| 59 | —CH₂CH₂— | CH₃ | CH₃ | H | H | H | N—N (pyridazine) | —COOCH₃ | 300 |
| 60 | —CH₂CH₂— | CH₃ | CH₃ | H | H | H | N—N | —COOCH₃ | 320–324 |
| 61 | —CH₂CH₂— | CH₃ | CH₃ | H | H | H | OH, N, N (pyrimidinol) | —COOC₄H₉ | 320 |

EXAMPLES 62–64

The pyrazolinones shown in Table 3 were prepared similarly to Example 17. In the event of poor solubility, either the mixture was refluxed or the reaction was catalyzed with 0.05 molar equivalent of trifluoroacetic acid. Instead of the extraction with ether, the reaction mixture was evaporated down and subjected to preliminary purification by column chromatography (silica gel; 95:5 n-hexane/ethyl acetate). The product was then recrystallized from ether/n-hexane or ethyl acetate/n-hexane.

TABLE 3

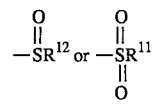

A

B

| Example | Formula | $R^3$ | $R^4$ | $R^5$ | $R^1$ | $R^6$ | mp. (°C.) |
|---|---|---|---|---|---|---|---|
| 62 | A | H | H | H | — | $-SO_2-CH_3$ | 246–248 |
| 63 | B | H | H | — | OH | $-SO_2-CH_3$ | 246–248 |
| 64 | B | H | H | — | OH | $-COOC_2H_5$ | 202–203 |
| 65 | A | H | H | H | — | $-SO_2-C_2H_5$ | 161–165 |
| 66 | A | H | H | H | — | $-SO_2-i-C_3H_7$ | 187–189 |

67: 1-(4-methanesulfonylphenyl)-4-(5,6,7,8-tetrahydro-5,5,8,8-tetramethyl-2-naphthalenyl)pyrazole, mp. 239–241° C., was synthesized as in Ex. 15.
68: 1-(4-methanesulfonylphenyl)-3-(5,6,7,8-tetrahydro-5,5,8,8-tetramethyl-2-naphthalenyl)-2-pyrazoline, mp. 234–236° C., was synthesized as in Ex. 16.
69: 5-(4-carboxyphenyl)-3-(5,6,7,8-tetrahydro-7-hydroxy-5,5,8,8-tetramethyl-2-naphthalenyl)isoxazole, mp. 289–291° C., was synthesized as in Ex. 18.
70: 2-(4-ethanesulfonylphenyl)-5-(5,6,7,8-tetrahydro-5,5,8,8-tetramethyl-2-naphthalenyl)pyrrole, mp. 254–257° C., was synthesized as in Ex. 10.
71: 2-(4-ethanesulfonylphenyl)-5-(5,6,7,8-tetrahydro-5,5,8,8-tetramethyl-2-naphthalenyl)furan, mp. 202–204° C., was synthesized as in Ex. 1.
72: 2-(4-ethanesulfonylphenyl)-5-(5,6,7,8-tetrahydro-5,5,8,8-tetramethyl-2-naphthalenyl)thiophene, mp. 183–185° C., was synthesized as in Ex. 9.

We claim:
1. Compounds of the formula I

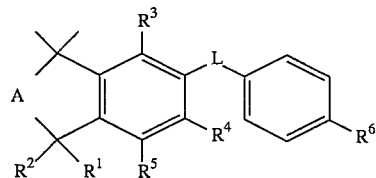

where $R^1$ and $R^2$ are each hydrogen or methyl, A is an ethylene or methylene radical which is unsubstituted or substituted by methyl, hydroxyl or oxo, L is

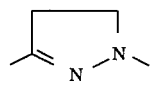

$R^3$ is hydrogen, a hydroxy or $C_1$-$C_6$-alkoxy group,
$R^4$ is hydrogen, $C_1$-$C_4$-alkyl, halogen or methoxy,
$R^5$ is hydrogen, methoxy or tert-butyl,
$R^6$ is hydrogen, methyl, nitrile or a $C_2$-$C_{10}$-ketal group or the group $-CHR^7OR^8$, $-CHR^7-NR^9R^{10}$, $-COR^{11}$, $-SR^{12}$, $$-\overset{O}{\underset{}{S}}R^{12} \text{ or } -\overset{O}{\underset{O}{S}}R^{11}$$

in which
$R^7$ is hydrogen or $C_1$-$C_4$-alkyl,
$R^8$ is hydrogen, $C_1$-$C_4$-alkyl or $C_1$-$C_{20}$-alkanoyl or is benzoyl which is unsubstituted or substituted by methoxy, nitro, methyl or chlorine,
$R^9$ and $R^{10}$ are each hydrogen, $C_1$-$C_4$-alkyl or $C_1$-$C_6$-alkanoyl or are each benzoyl which is unsubstituted or substituted as for $R^8$, or $R^9$ and $R^{10}$, together with the nitrogen atom to which they are bonded, form a saturated, 5-membered or 6-membered heterocyclic group which may contain oxygen as the second heteroatom,
$R^{11}$ is hydrogen, $C_1$-$C_4$-alkyl, $-OR^{13}$ or $-NR^{14}R^{15}$, where $R^{13}$ is hydrogen, unsubstituted or hydroxyl-substituted $C_1$-$C_8$-alkyl, aryl or aralkyl which is unsubstituted or substituted by chlorine, bromine, methyl, methoxy or nitro, substitution in the case of the aralkyl group being in the aryl moiety, and where $R^{14}$ and $R^{15}$ are each hydrogen, unsubstituted or hydroxyl-substituted $C_1$-$C_6$-alkyl or an aralkyl or aryl group which is unsubstituted or substituted as for $R^{13}$, or $R^{14}$ and $R^{15}$, together with the nitrogen atom to which they are bonded, form a heterocyclic group as defined above for $R^9$ and $R^{10}$, and $R^{12}$ is $C_1$-$C_4$-alkyl, or their physiologically tolerated salts.

2. A compound of the formula I as claimed in claim 1, wherein $R^6$ is nitrile, a $C_2$-$C_{10}$-ketal group or one of the radicals $-CHR^7-OR^8$, $-CHR^7-NR^9R^{10}$, $-COR^{11}$, $-SR^{12}$, $-S(O)R^{12}$ or $-S(O)_2R^{11}$.

3. A compound of the formula I as claimed in claim 1, wherein $R^6$ is a $C_2$-$C_{10}$-ketal group or one of the radicals $-COR^{11}$, $-SR^{12}$, $-S(O)R^{12}$ or $-SO_2R^{11}$.

4. A compound of the formula I as claimed in claim 1, wherein $R^6$ is one of the radicals $-COR^{11}$ or $SO_2R^{11}$.

5. A compound of the formula I as claimed in claim 1, wherein $R^9$ and $R^{10}$ together with the nitrogen atom to which they bonded form a pyrrolidino, piperidino or morpholino heterocyclic group.

6. A compound of the formula I as claimed in claim 1, wherein $R^{14}$ and $R^{15}$ together with the nitrogen atom to which they are bonded form a pyrrolidino, piperidino or morpholino heterocyclic group.

7. A drug or cosmetic for topical administration which contains, in addition to conventional pharmaceutical or cosmetic auxiliaries, from 0.0001 to 1% by weight of a compound of the formula I as claimed in claim 1 as an active compound.

8. A drug for systemic administration which contains, in addition to conventional pharmaceutical auxiliaries, from 0.1 to 50 mg, per single dose, of a compound of the formula I as claimed in claim 1 as an active compound.

\* \* \* \* \*